United States Patent [19]

Benson

[11] Patent Number: 5,814,050
[45] Date of Patent: Sep. 29, 1998

[54] HIP OFFSET-INSET APPARATUS AND METHOD

[75] Inventor: Gail M. Benson, Sioux Falls, S. Dak.

[73] Assignee: Bentwood Place, Inc., Sioux Falls, S. Dak.

[21] Appl. No.: 474,401

[22] Filed: Jun. 7, 1995

Related U.S. Application Data

[60] Continuation-in-part of Ser. No. 250,164, May 27, 1994, which is a division of Ser. No. 882,938, May 14, 1992, Pat. No. 5,318,571.

[51] Int. Cl.$^6$ .................................................. A61B 17/56
[52] U.S. Cl. .............................. 606/102; 606/91; 606/54
[58] Field of Search ..................... 606/91, 102, 54–59, 606/53, 87, 89, 96, 86; 623/22

[56] References Cited

U.S. PATENT DOCUMENTS

| | | | |
|---|---|---|---|
| 4,662,365 | 5/1987 | Gotzen et al. | 606/59 |
| 4,782,842 | 11/1988 | Fietti, Jr. | 606/54 |
| 4,988,349 | 1/1991 | Pennig | 606/59 X |
| 5,122,145 | 6/1992 | Fishbane | 606/102 |
| 5,318,571 | 6/1994 | Benson | 606/102 |

OTHER PUBLICATIONS

W.H. Harris, M.D., "A New Approach to Total Hip Replacement Without Osteotomy of the Greater Trochanter," *Clinical Orthopaedics and Related Research*, 1975, 106:19–26.

J. Edeen, et al., in "Clinical Significance of Leg–Length Inequality After Total Hip Arthroplasty".

W.H. Harris, M.D., "Revision Surgery for Failed Nonseptic Total Hip Arthroplasty," *Clinical Orthopaedics and Related Research*, 1982, 170:8–20.

W.E. Knight, M.D. ("Accurate Determination of Leg Lengths During Total Hip Replacement," *Clinical Orthopaedics and Related Research*, 1977, 123:27–28.

N.M.J. McGee, F.R.C.S., et. al., "A Simple Method of Obtaining Equal Leg Length in Total Hip Arthroplasty," *Clinical Orthopaedics and Related Research*, 1985, 194:269–270.

S.T. Woolson, M.D., et. al., "A Method of Interoperative Limb Length Measurement in Total Hip Arthroplasty," *Clinical Orthopaedics and Related Research*, 1985, 194:207–210.

*Primary Examiner*—Robert A. Hafer
*Assistant Examiner*—Benjamin K. Koo
*Attorney, Agent, or Firm*—Fredrikson & Byron, P.A.

[57] ABSTRACT

An apparatus and method for determining offset-inset distances in the course of a total hip arthroplasty procedure. The apparatus includes a first attachment attachable to the superior eminence of the acetabulum, a second attachment point capable of being fixed to the femur at approximately the position of the greater trochanter, and preferably, a measuring device for measuring and noting the distance between the reference point and either the third or fourth fixed points.

15 Claims, 9 Drawing Sheets

HIP OFFSET-INSET APPARATUS AND METHOD

TECHNICAL FIELD

The present invention relates to a method and apparatus for facilitating a total hip arthroplasty procedure in which both an acetabular cup prosthesis and a femoral implant prosthesis are installed, or a partial hip arthroplasty where one of the components of an earlier arthroplasty are replaced. In particular, the invention relates to a method and apparatus for assuring that the resulting leg length and hip offset of the patient is optimized.

RELATED APPLICATIONS

The present application is a continuation-in-part of U.S. Ser. No. 08/250,164, filed May 27, 1994, which is a divisional application of U.S. Ser. No. 07/882,938, filed May 14, 1992 and issued Jun. 7, 1994 as U.S. Pat. No. 5,318,571 for a "Method and Apparatus for Simplifying Total Hip Arthroplasty".

BACKGROUND OF THE INVENTION

Total and replacement arthroplasty procedures employing artificial acetabular cup prostheses and femoral implants have been performed for a great many years. The installation of a replacement hip joint prosthesis involves surgically exposing and dislocating the joint, cutting away the head and neck and a portion of the greater trochanter in a femoral neck resection, and reaming the femoral canal to accept the metallic stem of the femoral implant.

Femoral implants are available in a variety of lengths and cross-sectional dimensions to fit the shape of the reamed-out femoral canal. Such implants are also provided with an angularly disposed femoral neck and spherical head that extend at an angle to the stem to orient the replacement head in the acetabular cup prosthesis. The acetabular cup prosthesis is itself installed in the patient's reamed-out acetabulum. After both components are installed, the spherical head is inserted into the cup and the muscles and tendons that were separated or severed in the surgical exposure are reattached to hold the leg in place.

Numerous articles have been published describing and illustrating total hip arthroplasty procedures employing a wide variety of total hip joint prostheses. For example, the publication entitled "Total Hip Arthroplasty Using a Universal Joint Device," by Raymond G. Tronzo, M.D., published in 1970 by Richards Manufacturing Company, 1450 Brooks Road, Memphis, Tenn. 38116, describes such a procedure employing the products of the Richards Manufacturing Company. A further brochure entitled "PERFECTA Femoral Prostheses With T-MATRIX Acetabular Options—Surgical Protocol," published in 1990 by Orthomet, Inc., Minneapolis, Minn., describes and illustrates the surgical procedure employed in installing Orthomet products. Other manufacturers publish similar instruction manuals or protocols for their products.

A common problem that arises in completing the total hip arthroplasty procedure involves the selection of the appropriate length neck of the femoral implant so that after the procedure is completed, the patient enjoys a normal or enhanced leg length. The differences in leg length arise from the difference in sizes of the femoral implants, the depth of insertion of the acetabular cup, and the length of the reducted femoral neck. To change the length of a leg, surgeons often simply change the length of the femoral neck that is used. Once the acetabular cup is in place, the cup itself is rarely changed.

J. Edeen, et al., in "Clinical Significance of Leg-Length Inequality After Total Hip Arthroplasty" provides a summary of interviews and examinations of 68 patients after total hip arthroplasty. Their findings confirm that there was a high rate of dissatisfaction among patients, particularly due to leg-length inequality. The authors refer to various methods available to surgeons for equalizing leg lengths intraoperatively, but were unable to validate any particular method.

A variety of methods have been used to estimate the length of the leg upon implanting a new femoral implant and acetabular cup. Some methods have involved measuring the distance from the palpable iliac crest near the waist line to the greater trochanter on the outside of the proximal femur, both of these markers are quite distant from the true hip joint and only indirectly attempt to measure length.

Other methods described in the literature measure the distance from an anchor installed percutaneously above the superior acetabulum to a marker on the exposed greater trochanter. See, for example, S. T. Woolson, M.D., et. al., "A Method of Interoperative Limb Length Measurement in Total Hip Arthroplasty," *Clinical Orthopaedics and Related Research*, 1985, 194:207–210; W. H. Harris, M.D., "Revision Surgery for Failed Nonseptic Total Hip Arthroplasty," *Clinical Orthopaedics and Related Research*, 1975, 106:19–26; and N. M. J. McGee, F.R.C.S., et. al., "A Single Method of Obtaining Equal Leg Length in Total Hip Arthroplasty," *Clinical Orthopaedics and Related Research*, 1985, 194:269–270.

In an article by W. E. Knight, M.D. ("Accurate Determination of Leg Lengths During Total Hip Replacement," *Clinical Orthopaedics and Related Research*, 1977, 123:27–28), a tool is described for measuring the distance between bone screws placed in the exposed ilium about two inches above the margin of the acetabulum and in the greater trochanter of the femur in line with the iliac screw in the coronal plane. The tool is positioned laterally to the pins and the measurement is made parallel to the femur, which is not necessarily parallel to the weight-bearing axis.

These methods are flawed as they measure two dimensions, length (vertical dimension) plus lateralization (horizontal translation of the femur). The hip and leg position must be virtually identical when pre-operative and post-operative measurements are made to insure predictable results. In practice, the horizontal offset and leg position have traditionally been difficult to replicate. Accordingly, better surgical procedures for obtaining exact leg length and hip offset are to be desired.

Copending application U.S. Ser. No. 08/250,164, the disclosure of which is incorporated herein by reference, describes a method and apparatus for use in surgical hip replacement procedures for ensuring that the replacement hip joint components are properly sized so that the resulting length of the patient's leg is correct. In the procedure, when the acetabulum and femur are exposed, one end of a flexible measuring cable is attached to the superior eminence of the acetabulum and the cable is extended inferiorly so that it is aligned with a specific point on the femur, preferably the lesser trochanter.

The selected point on the femur is marked and the scaling or marking indicator carried by the flexible cable is positioned in relation thereto. After this reference distance between the fixed points on the acetabulum and the femur is determined, the flexible cable is moved out of the way while its end remains fixed to the acetabulum.

Thereafter, the total hip arthroplasty procedure continues in the usual fashion with the installation of an acetabular cup prosthesis and the femur is prepared to receive the femoral implant. After the femur is prepared, trial femoral implants are installed to determine the proper fit with the femoral canal. The selection of the proper neck length to ensure the proper resulting leg length is facilitated by extending the flexible cable attached at one end to the superior eminence of the acetabulum toward the marked position of the femur so that the marked position is aligned with the indicator fixed to the cable.

The art is still need of methods and articles for accurately restoring not only normal joint length, but also the center of hip rotation and femoral offset at the time of hip replacement. This ability is necessary in order to reduce problems such as dislocation-subluxation, and polyethylene wear that can lead to joint erosion and loosening, as well as leg length inequality. In turn, the ability to reduce such problems will improve mechanical function and patient satisfaction.

SUMMARY OF THE INVENTION

In one aspect, the present invention provides a method of reconstructive hip surgery involving the replacement of a dysfunctional hip joint with a total hip prosthesis, the method comprising the steps of:

(1) providing a hip length device for marking and measuring a pre-replacement length distance between two fixed points along the weight bearing axis of the joint;

(2) providing a femoral offset-inset apparatus for marking third and fourth fixed points and for measuring pre-replacement distances between these points and a first reference point positioned in a medial dimension with respect to the joint;

(3) surgically exposing the superior portion of the femur and the acetabular region of the iliac bone;

(4) employing the hip length device to mark a first fixed point in the acetabular region of the iliac bone and a second fixed point on the lateral portion of the exposed femur, and measuring the pre-replacement length distance between the first and second points with the femur normally extended;

(5) employing the offset-inset apparatus to mark a third fixed point on the medial portion of the exposed femur, and to provide a fixed reference point in a medial position with respect to the third fixed point, and measuring an offset distance between the fixed reference point and the third point with the hip in a reproducible, restrained position, (6) performing the surgical procedure of a hip dislocation and removal of the femoral head in order to expose the surface of the acetabulum;

(7) employing the offset-inset apparatus to identify a fourth fixed point on the surface of the exposed acetabulum, and to measure an inset distance between the fixed reference point and the fourth point with the hip in a reproducible, restrained position;

(8) determining a suitable proximal femoral width as the difference between the measured inset and offset distances, and selecting a femoral component with an appropriate offset dimension corresponding thereto;

(9) performing the surgical procedure of implanting a trial acetabular prosthesis and employing the offset-inset apparatus to measure the post-replacement inset distance;

(10) performing the surgical procedure of preparing the femur and inserting a trial femoral component;

(11) employing the offset-inset apparatus to recheck the offset distance between the third mark and the reference point to provide the desired post-replacement dimensions; and (12) employing the hip length device to recheck the distance between the first and second marks to provide desired post-replacement joint length.

In a preferred embodiment, the offset-inset apparatus shares one or more components in common with the hip length device. In particular, the fixed ileac marker of the hip length device is provided in the form of an extended post or other suitable form. The post, in turn, is capable of serving as an anchor point for establishing the fixed reference point of the offset-inset apparatus.

The ability to use a single fixed marker in both the hip length and offset/inset measurements greatly facilitates the ease and accuracy of the present method. This ability also serves to alleviate unnecessary trauma to the body, by minimizing the number and location of fixed markers.

In another aspect, the invention relates to an offset-inset apparatus, which may be in kit form, for performing the surgical procedure. The invention involves an offset-inset apparatus which comprises a first attachment attachable to the superior eminence of the acetabulum. The first attachment can be fixed directly to the bone, but preferably is indirectly fixed by attachment to a fixed point provided by the hip length apparatus. The offset-inset apparatus further involves a second attachment point capable of being fixed to the femur at approximately the position of the greater trochanter. Optionally, and preferably, the apparatus further includes a measuring device for measuring and noting the distance between the reference point and either the third or fourth fixed points.

BRIEF DESCRIPTION OF THE DRAWING

These and other advantages and features of the present invention will become apparent from the following detailed description of the preferred embodiments thereof in conjunction with the Drawing in which.

DETAILED DESCRIPTION

The method and apparatus of the present invention can be used to provide pre- and corresponding post-operative measurements of joint length and joint offset-inset dimensions, thereby substantially eliminating problems due to incorrect sizing of components, and in turn, the need to reoperate.

Using the presently described apparatus and method in the surgical field, pre-replacement length, center of rotation and femoral offset can be accurately measured. The position of the calcar cut, the reaming of the acetabulum, and the selection of the type of prosthesis in regard to head-neck length, femoral neck angle and built in offset can be accurately guided by serial measurements during replacement. At the conclusion of the procedure a stable hip of correct length, and having close to normal anatomic geometry, can be expected. Improved function of the hip as well as lower rates of dislocation, leg length disparity, polyethylene wear and revision surgery can be expected. These devices can be expected to aid the joint manufacturers in development of new prosthesis.

Figure 1:
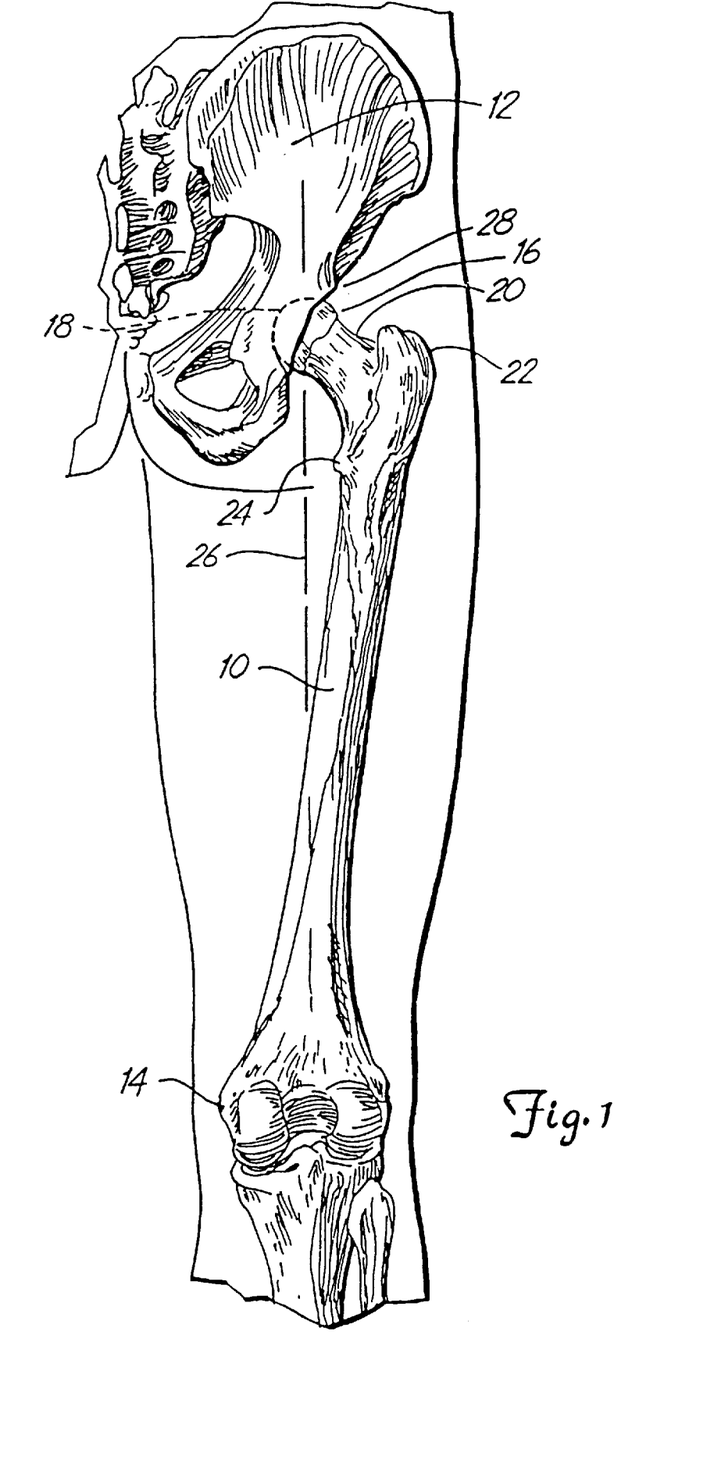
FIG. 1 is a posterior view of the right pelvic girdle and a portion of the right leg bones.

Turning now to the Drawing and first to FIG. 1, it illustrates a posterior view of the right pelvic girdle and a portion of the right leg showing the normal alignment of a human hip joint in relation to the knee joint. The femur 10, or thigh bone, articulates at its proximal end with the iliac bone 12. Its distal end articulates with the tibia at the knee joint 14. The shaft of the femur bows medially so that it approaches the femur of the opposite thigh. As a result of this convergence, the knee joints are brought together to the body's line of gravity or weight supporting axis.

The proximal end of the femur 10 comprises the rounded head 16 that articulates with the acetabulum 18 of the iliac bone 12. The neck 20 of the femur 10 is a constricted region distal to the head 16. A fairly common fracture in the elderly occurs at the neck 20. Apparently the neck 20 becomes so weak that it fails to support the body. The greater trochanter 22 and lesser trochanter 24 are projections on the femur 10 that serve as points of attachment for some of the thigh and buttock muscles.

Between the trochanters on the anterior surface is a narrow introchanteric line. Between the trochanters on the posterior surface is an intertrochanteric crest. The shaft of the femur contains a rough vertical ridge on its posterior surface called the linea aspera. This ridge serves for the attachment of several thigh muscles. The distal end of the femur is expanded and includes the medial condyle and the lateral condyle. These articulate with the tibia and (with attendant ligaments, etc.) from the knee joint 14.

The weight of the body is borne by the normal pelvic girdle and lower extremities in conjunction with the associated muscles and ligaments in a weight supporting axis extending generally through the superior aspect of the acetabulum 18 inferiorly alongside the femur and through the center of the knee joint 14 generally as illustrated by broken line 26 in FIG. 1. The weight supporting axis 26 passes through or adjacent to a line draw in between the superior eminence 28 of the acetabulum and the lesser trochanter 24.

Through disease processes or injury, the hip joint may become less mobile, painful or totally unusable, requiring surgical intervention and a total hip arthroplasty employing a hip joint prosthesis of the type described in the above-referenced publications. A wide variety of prostheses are available from several manufacturers, the prostheses typically including a metal acetabular cup for surgical replacement of the natural acetabulum 18, a high density polyethylene cup liner positioned within the cup prosthesis and a femoral implant comprising a femoral stem and a femoral ball-shaped head of the type illustrated in FIG. 2.

Figures 2, 3:
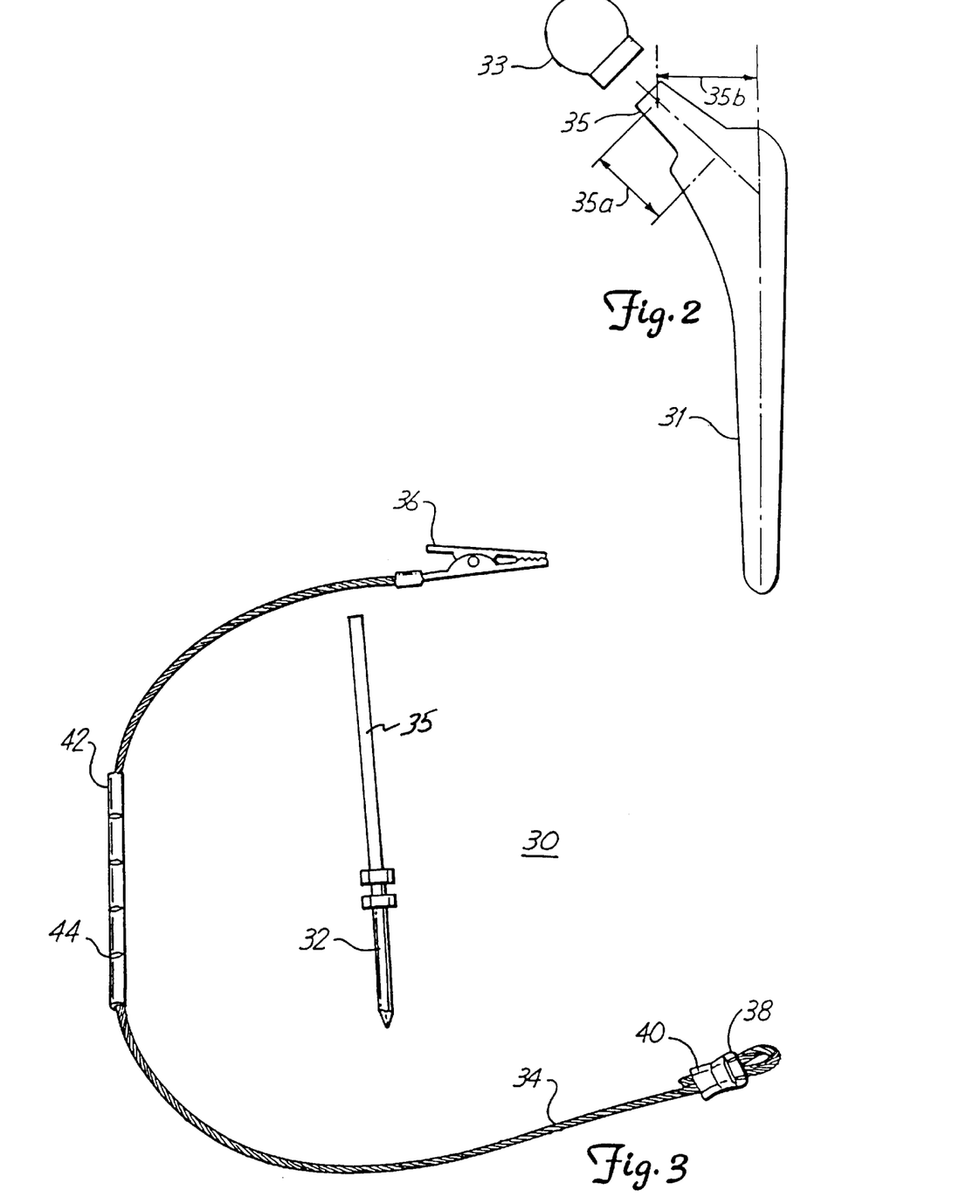
FIG. 2 is an illustration of a femoral implant of a type employing a separate head adapted to fit in an acetabular cup of a total hip joint replacement prosthesis.
FIG. 3 is an illustration of a first embodiment of a hip length apparatus modified of the type described in co-pending U.S. application Ser. No. 08/250,164.

Turning now to FIG. 2, it illustrates a typical femoral implant stem 31 and femoral implant head 33 which are attached together to form the femoral implant 29. The femoral stem 31 is available in a number of cross-section shapes, sizes and lengths having varying exterior contours, neck offsets and neck lengths. The femoral implant head 33 is usually a highly polished, spherical metal ball provided in a number of available diameters and neck lengths and provided with a Morse taper female receptacle for receiving the Morse tapered neck 35 of a stem 31. In practice, manufacturers of total hip prostheses provide a selection of different neck length femoral implant stems 31 and femoral implant heads 33. Thus, it is possible to customize the overall neck length as necessary to replicate the proper leg length for the individual patient.

As described above, upon completion of the operative procedure, it has often been found that the overall leg length and/or offset dimension is incorrect, requiring a reoperation, usually involving replacement of one or both of the components of the femoral implant. The operative procedure can be simplified and the need to reoperate substantially eliminated by providing a measurements of both joint length and the offset-inset dimensions both prior to and following the implantation of trial components.

To this end, FIG. 3 illustrates a preferred hip length device for marking and measuring a pre-replacement length distance between two fixed points along the weight bearing axis of the joint. A suitable hip length device involves (a) a first marker nail in the form of a post for providing fixed attachment to the superior eminence of the acetabulum, (b) a length of flexible cable attachable at a fixed end to the post, (c) one or more markers moveable along the length of the cable, and (d) a second marker nail for marking a fixed position on the lesser trochanter.

In a preferred embodiment, the hip length device is of the type described in co-pending application Ser. No. 08/250, 164. In a particularly preferred embodiment, the marker used to provide fixed attachment to the superior aspect of the acetabulum is provided in the form of a post. The post can be of any form and dimensions suitable to allow it to serve as the anchor point for establishing a reference point medial to the greater trochanter.

Figure 4:
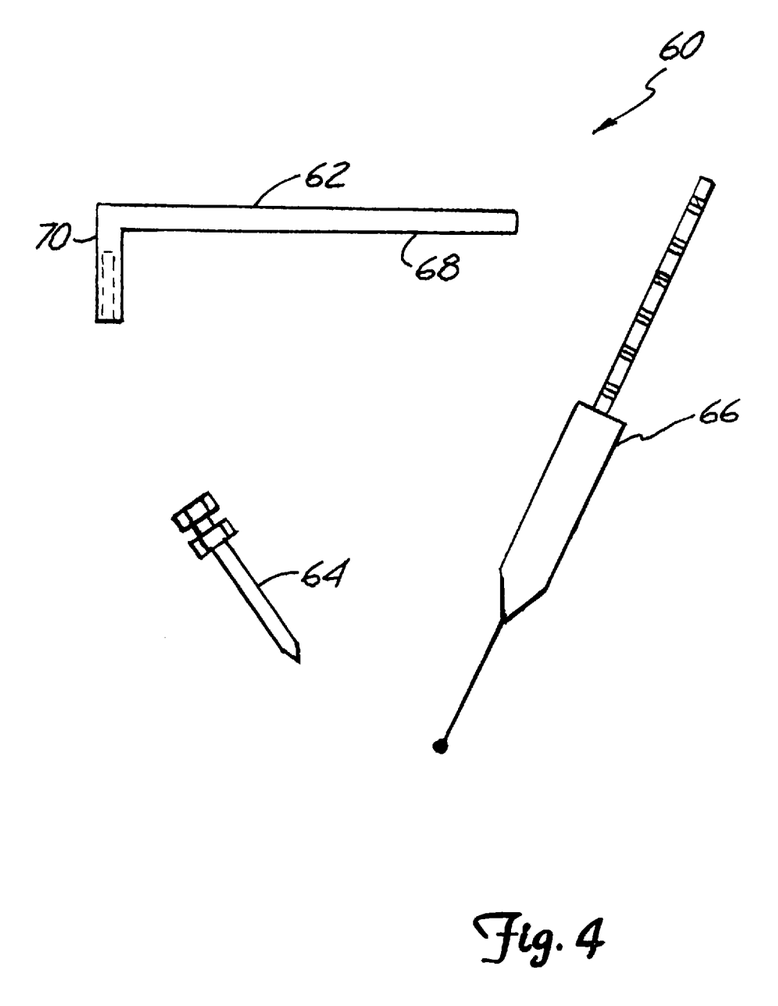
FIG. 4 is an illustration of a first embodiment of an offset-inset apparatus employed in the practice of the method of the present invention.

FIG. 3 illustrates a preferred hip length apparatus 30 comprising length of cable 34 and a bone nail 32, the form of an elongated tower, that are used to select a properly sized femoral stem 31 and head 33 during the procedure and avoid reoperation. The hip length apparatus depicted in FIG. 3 comprises a length of stranded wire cable 34 extending between an alligator clip 36 and a loop 38 formed by bending the cable 34 back against itself and crimping a crimp tube 40 around both to form a loop. The loop 38 is formed after the bone nail 32 is fixed in the region of the superior eminence 28 of acetabulum 18 as shown in FIG. 4. The alligator clip 36 is provided so that the free end of the cable 34 may be attached to a surgical drape to hold the apparatus 30 out of the surgical field when it is not used in the manner depicted in FIGS. 5 and 6.

The hip length apparatus 30 also includes one or more slidable tubes (e.g., as shown by reference number 42) having four calibration marks 44 spaced apart about one centimeter in the outer surface of the tube 42. The calibration tube 42 may be slid back and forth on the length of stranded wire cable 34 so that one of the marks 44 is aligned with a mark or attachment, e.g., another bone nail 46, made on the femur 10 and crimped in place by a crimping tool.

In a preferred embodiment the tower portion of nail 32 is of sufficient length and configuration to allow the rigid attachment of a removable rod extending in a substantially perpendicular position. The rod, in turn, can be directed into a position medial to the greater trochanter to provide a reference point for offset-inset measurements.

Turning now to FIG. 4, it illustrates a preferred offset-inset apparatus 60 of the present invention, comprising a removable rod 62, a third bone nail 64. Optionally, the apparatus depicted in FIG. 4 further comprises a separate measuring device 66, e.g., in the form of a depth gauge, useful for determining the inset and offset distances between the fixed reference point and the fourth nail and the exposed acetabular cup, respectively. The depth gauge can include a barrel portion capable of being grasped, together with a slidable distance probe, the movement of which corresponds with the appearance of distance or reference markings identifiable above the barrel of the gauge.

A reference point can be formed in any suitable manner to provide a fixed, reproducible reference point in a position medial to the femur. In a preferred embodiment the reference point is formed from, and anchored to the nail used to form a fixed acetabular position for the hip length device.

The rod 62 is capable of being attached to the tower portion of bone nail 32 of the hip length device in order to form a fixed, reproducible reference point in a position medial to the original position of the greater trochanter. In the embodiment illustrated, for instance, rod 62 is formed of a longitudinal arm portion 68 and a perpendicular attachment portion 70. As described below, attachment portion 70 can be attached to the tower portion of first bone nail 32 in any suitable manner, e.g., by providing a female attachment site for the tower portion.

The relative dimensions or shapes of the bone nail 32 and rod 62 are not critical, nor is the means of attaching the rod to the post, so long as together they capable of reproducibly forming a fixed point in space that is medial to the original position of the greater trochanter. The third bone nail 64 is capable of being fixed in the region of the greater trochanter in order to form a fixed point for measurement of the offset distance to the fixed reference point. The measuring device can also be provided in any suitable form, e.g., as a depth gauge capable of being held beside the third or fourth reference points to visually determine the distance to the reference point.

Figure 5:
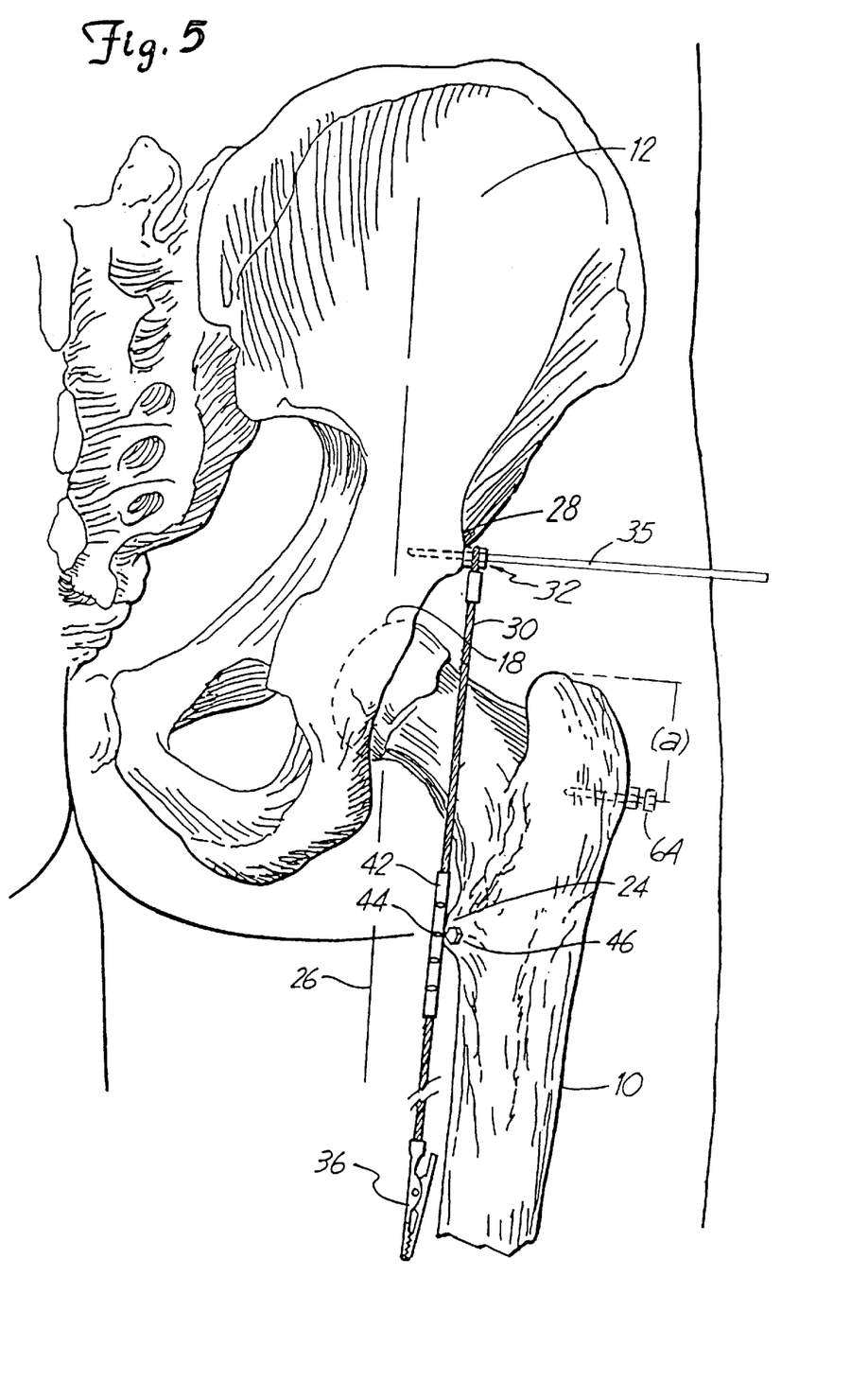
FIG. 5 is an illustration of the use of the hip length apparatus of FIG. 4 in initially measuring the distance between points on the iliac bone and the femur in a posterior surgical approach.

Referring to FIG. 5, a surgical procedure is performed in order to expose the superior portion of the femur and the acetabular region of the iliac bone. Prior to surgery, and using pre-operative X-rays of the pelvis, the surgeon can initially estimate the medialization of the acetabulum caused by arthritic erosion of the medial acetabular wall, or other causes. The surgeon can then estimate the amount of hip length lost by erosion of the articular cartilage, femoral head and acetabulum.

The method of the present invention will be described with respect to the posterior approach, which Applicant has found to be a preferred approach due to the technical ease in measuring the three variables of hip length, center of rotation and femoral offset. In practice, the procedure may be used in an anterior surgical approach as well. Selection of the anterior or the posterior approach is left to the discretion of the surgeon. Those skilled in the art will appreciate the manner in which the anterior or transtrochanteric approach can also be done with minor surgical modifications to the procedure as well.

The tensor fascia lata is dissected and the hip external rotators are exposed. In a preferred embodiment, the typical external rotator release is modified by also releasing the quadratus femoris as well as the usual rotator release. This allows exposure of the lesser trochanter, which is crucial to allow accurate length measurement. The lesser trochanter is exposed by extreme internal rotation of the femur short of dislocation. A posterior hip capsulectomy is performed in routine fashion combined with a anterior capsulotomy and hemostasis is obtained.

A hip length device, of a modified type described in the co-pending U.S. application, is then employed to measure a pre-operative length distance. Removal of a segment of the glenoid labrum posterior superiorly allows clear visualization of the superior articular surface of the acetabulum. A modified Taylor retractor can be placed under the gluteus medius and minimus muscle to allow exposure of the supraacetabular area posterior and superiorly in an area 3–4 cm proximal to the acetabular rim.

The hip length device is used to mark a first fixed point in the acetabular region of the iliac bone and a second fixed point on the lateral portion of the exposed femur. FIG. 5 illustrates the placement of the hip length apparatus 30 to effect a calibrated measurement of distance along the weight supporting axis 26 between the femur 10 and the iliac bone 12 before the head 16 is dislocated from the acetabulum 18.

It will be understood that for the sake of simplicity, the operating field, including the incision and the separation of the muscles and ligaments, are not illustrated in the Figures. Assuming that those operative steps have been taken, the proximal end of the femur 10 and the portion of the iliac bone 12 surrounding the acetabulum 18 are exposed.

A first marker nail 32 is provided, preferably in the form of a cylindrical post with an attached length cable and a depth stop. The first marker can be drilled or otherwise impacted into the supraacetabular area, posterior-superiorly approximately 2 cm proximal to the roof of the acetabulum at the 11 o'clock or 1 o'clock positions relative to the face of the acetabulum and dependent on which hip is being operated on. Recalling that the reflected head of the rectus femoris is at the 12 o'clock position superior to the acetabulum, care must be taken to place the tower on the vertical axis in both planes.

As shown in the Figure, the surgical nail 32 is driven into the region of the superior eminence 28 of the acetabulum 18 about 2 centimeters above the acetabular rim in the 11 o'clock position after the loop 38 in the cable 34 has been mechanically attached to the shaft of the nail 32. Thereafter, the cable 34 is extended in the direction of the weight supporting axis 26 bringing it alongside the lesser trochanter 24.

Then, as shown in FIG. 5, the slidable calibration tube 42 is moved along the length of cable 34 until one of its indicia 44 is aligned with a mark or nail 46 on the lesser trochanter 24. The mark is typically a further surgical nail driven into the bony protuberance of the lesser trochanter 24 since it is difficult to otherwise mark the bone.

As shown in FIG. 5, a second marker nail 46 (e.g. 1 cm in length) is inserted into the posterior aspect of the lesser trochanter, being careful not to penetrate the main femoral intramedullary canal. With the foot restrained in a foot holder and the knee extended, a third marker nail 64 is implanted, for later use in measuring hip offset distance. The third marker nail, approximately 1 cm in length, is placed in the prominence of the greater trochanter approximately 5 cm (distance "a") from the proximal end and once again in the vertical plane. Solid fixation in the trochanter is confirmed.

After the indicia 44 and nail 46 are aligned, the tube 42 is crimped tightly against the stranded wire cable 34 so that it cannot be moved or dislodged. With the leg restrained in the foot holder, a retractor can be used to visualize the lesser trochanter and the cable strung tightly from the tower to the marker on the lesser trochanter, the sliding scale is crimped at the middle mark at the level of the lesser trochanter marker nail. The selected indicia 44 is noted in the surgical record, as the pre-replacement length distance, and the cable 34 is pivoted superiorly out of the operating field.

The alligator clip 36 is attached to a surgical drape covering the patient's torso in order to keep the apparatus 30 out of the surgical field to allow the surgeon to proceed with offset-inset measurements. In particular, the surgeon will dislocate the head 16 from the acetabulum 18 and proceed with the resection of the femur and the surgical placement of the acetabular cup prosthesis and the reaming of the femoral canal to accept the trial femoral components.

Figure 6:
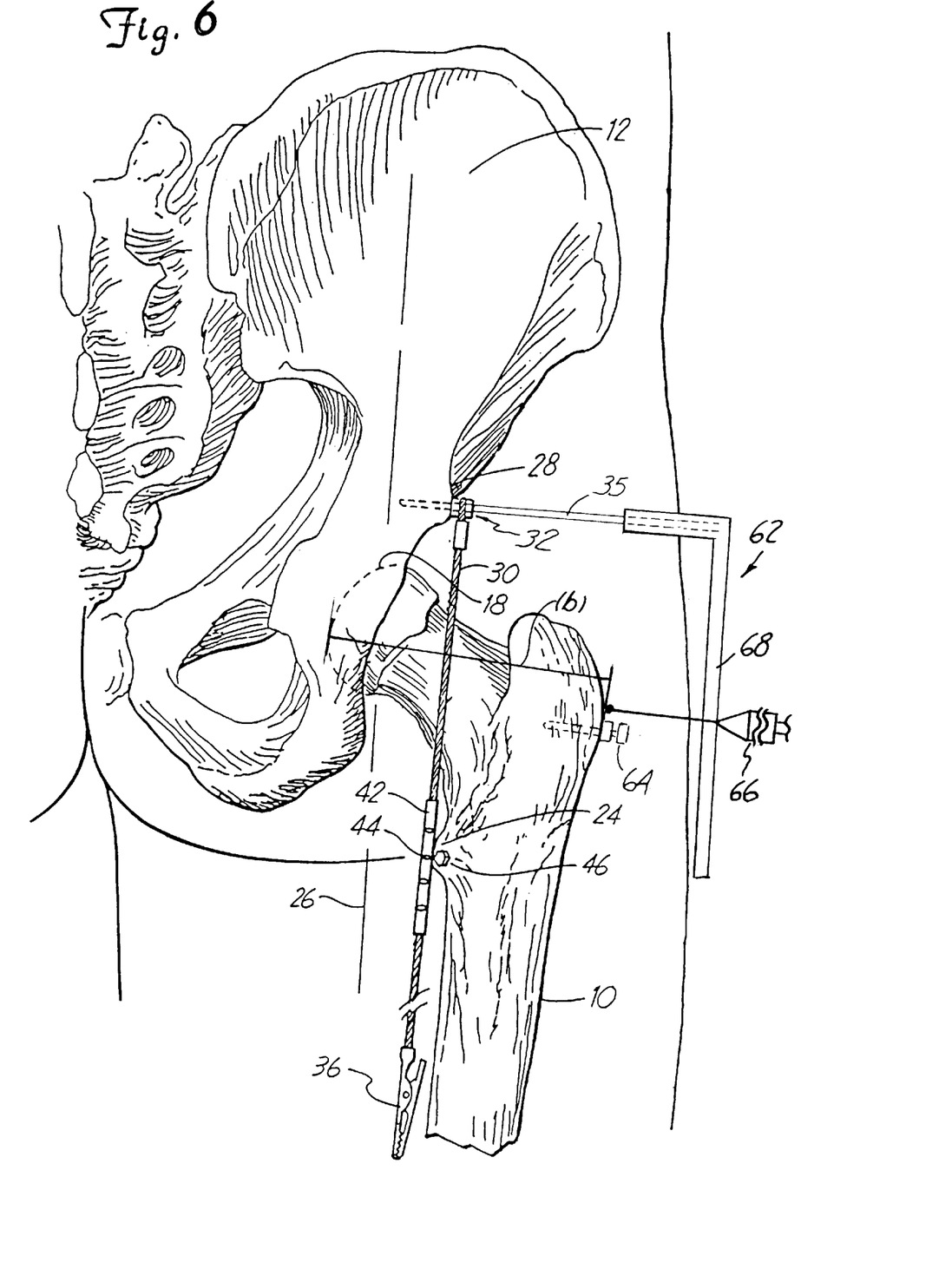
FIG. 6 is an illustration of the use of the offset-inset apparatus of FIG. 3 in measuring the offset distance between a reference point and the greater trochanter of the femur in a posterior surgical approach, showing the restrained position of the foot with respect to the operating table.

As shown in FIG. 6, a hip offset-inset device 62 of the present invention can then be employed to use the third marker nail previously marked on the lateral portion of the exposed femur.

In the course of measuring pre- and post-operative inset and offset distances, the patients foot is most preferably positioned in a fixed, reproducible position in space, above the operating table. Fixing the foot position aids the accuracy of this device, since factors such as variable leg position can significantly change the measurements.

In a preferred embodiment, a leg holding device is employed that comprises a holding boot and an attachment apparatus for holding the boot in a fixed position with respect to the surgical table. The leg is placed in the holding boot and the boot is attached to the leg holder in neutral position in regard to flexion-extension, abduction-adduction and rotation. The boot can be easily removed from the leg holder and is not attached to it during the procedure except at times measurements are being made.

With the patient in the customary lateral position and maintained by a standard McGuire-type frame, a standard incision is made. Those skilled in the art will understand that the incision can be a lateral, anterolateral or posterolateral one, depending on the surgeons preference and surgical approach.

In a preferred embodiment, the fixed reference point is formed by placing a removable rod portion 68 on the tower portion of nail 32 of the length device. The rod portion can be attached to the nail in any suitable manner, for instance, by forming a perpendicular angle portion 70 that can be connected to the tower by the use of a slip-fit coupling, a male-female threaded coupling, a serrated coupling, a locking collar, and the like.

The respective lengths of the bridge portion 35 and angle portion 70 are not critical, so long as the combined length once coupled is sufficient to allow the rod portion 68 to extend a sufficient distance medial to the femur. The length of the tower of nail 32 is preferably sufficient to terminate the tower about 3 cm lateral to the lateral trochanteric surface. The rod portion 68 is of sufficient length so that the depth gauge 66 can be laid aside its distal extension and onto the greater trochanteric nail 64, or preferably onto a point on the bone just above the marker nail.

With the depth gauge 66 contacting the bone above the greater trochanteric nail marker 64 the length of the offset is measured. This length is recorded for later use.

Alternatively, means other than a calibrated depth probe can be employed for determining the offset distance. For instance, using a nail that is itself calibrated along its tower portion, the rod can itself be moved laterally to a point where it contacts the bone above the head of the greater trochanteric nail. At that point, the corresponding location of the rod along the tower can be noted and the rod temporarily removed. Later, the rod can be used to measure the inset distance, by using a depth probe that extends down from the rod into the acetabulum. The distance can be determined by calibrations on either the probe or, if the rod is moveable along the tower, on the tower itself.

Figure 7:
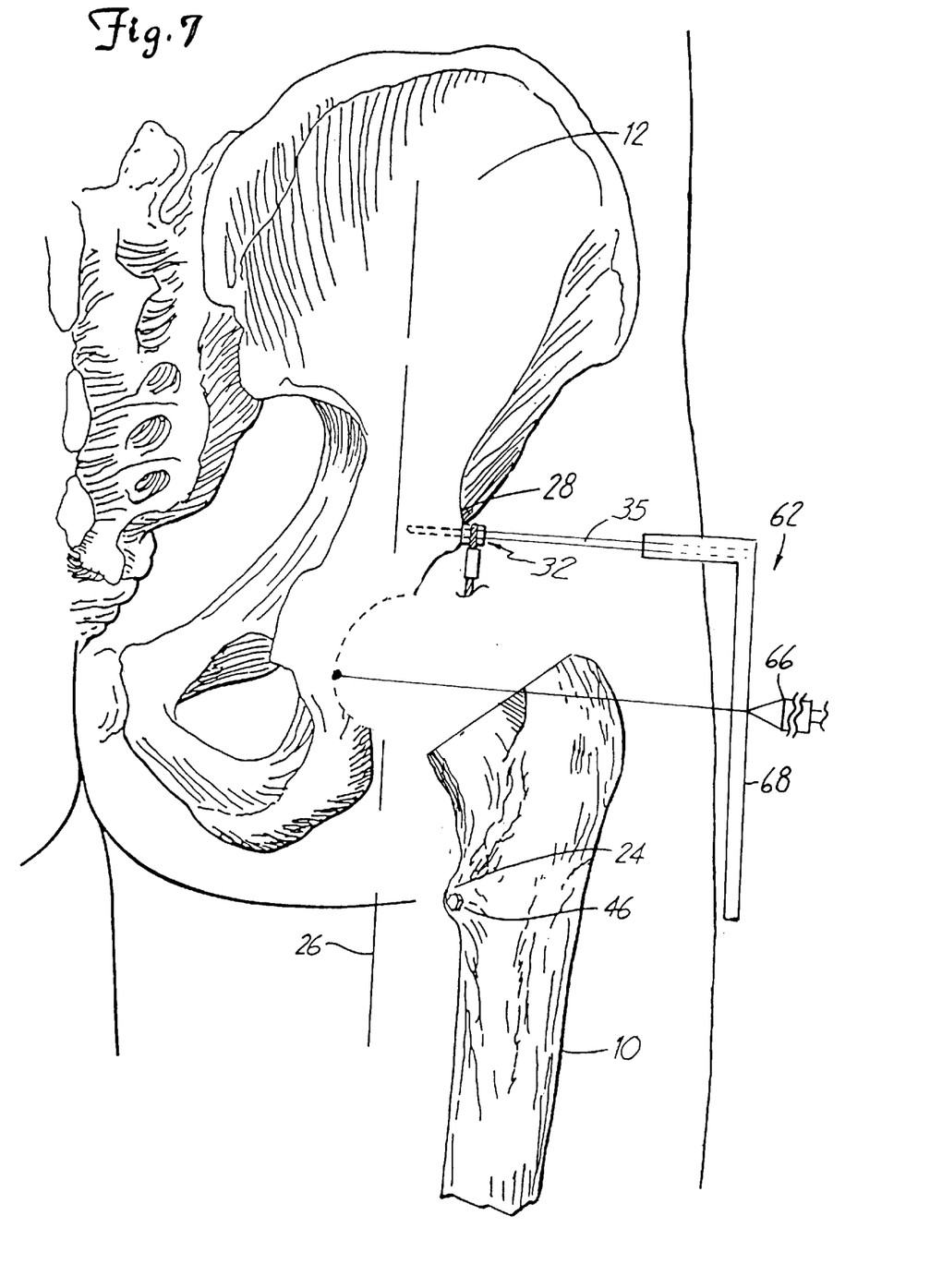
FIG. 7 is an illustration of the use of the offset-inset apparatus of FIG. 3, following hip dislocation, in initially measuring the inset distance between a reference point and the exposed acetabular surface.

Turning next to FIG. 7, following the pre-operative offset measurement, a further surgical procedure is performed to dislocate the hip and remove the femoral head in order to expose the surface of the acetabulum. In the surgical procedure, the foot is first removed from the foot holder, the hip dislocated and the neck divided at the appropriate level as estimated by the appropriate prosthetic head neck device, usually approximately 2 cm proximal to the lesser trochanter. The head is removed and the hip is internally rotated while retractors are placed anterior and posterior to the acetabulum to adequately expose its anatomy.

Thereafter, the offset-inset apparatus 62 is used to measure an inset distance between the reference point formed by bridge 68 and a fourth point on the surface of the exposed acetabulum with the hip in a reproducible, restrained position. With the foot placed back in the foot holder, and bridge 68 positioned on the tower portion of nail 32, the depth gauge 66 is dropped into the acetabulum to measure its depth.

The fourth fixed point can be visually identified by selecting an appropriate spot for the depth gauge to contact the medial acetabular wall. The fixed point can be anterior, superior or posterior to the fossa ovalis, but preferably not in the depth of the fossa. Measurement of the inset distance between rod 68 and the fourth fixed point determines the preoperative articular joint depth of the hip. The inset measurement can also be recorded for later use.

The difference between the inset and offset distances can be used to determine a suitable proximal femoral width (identified as distance "b" in FIG. 6), and to then select a femoral component with an appropriate offset dimension corresponding to that width. The surgeon can then perform the surgical procedure of implanting a trial acetabular prosthesis and employing the offset-inset apparatus to measure the post-replacement inset distance.

Figure 8:
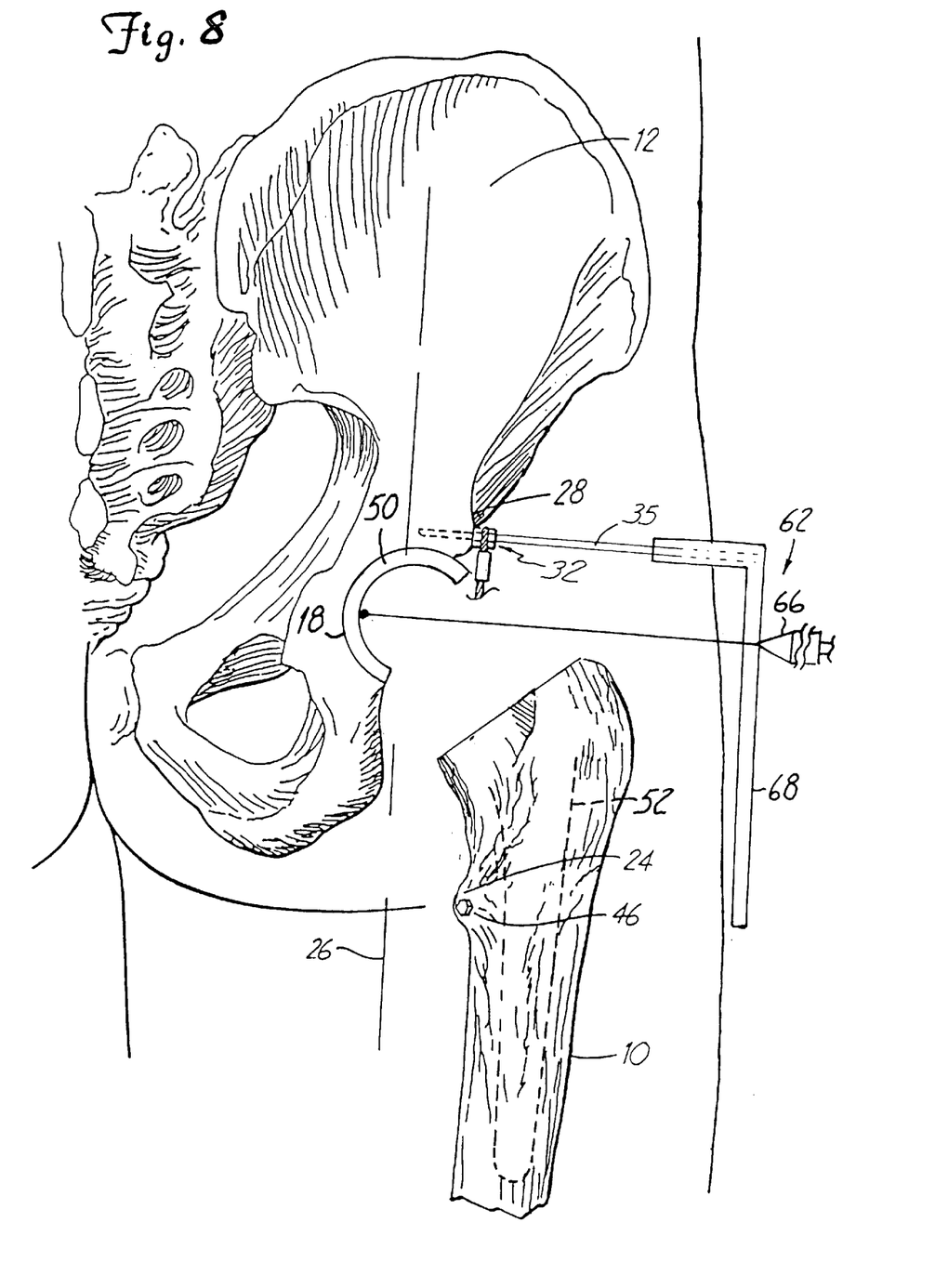
FIG. 8 is an illustration of the use of the offset-inset apparatus of FIG. 3, following the implantation of an acetabular cup component, for rechecking the inset distance in accordance with the method of the present invention practiced in a posterior surgical approach.

Turning now to FIG. 8, it illustrates the placement of an artificial acetabular cup prosthesis 50 in the location of the acetabulum 18. As the acetabulum is the first to be replaced, the appropriate reaming depth will be determined by factors such as the thickness of the acetabular prosthesis and the amount of erosion of the medial wall by the arthritis. If the opposite hip is normal, the estimations will be more accurate. The acetabulum is then reamed to the appropriate depth, repeatedly checking the inset measurement as the reaming proceeds. In some cases with a genetically thin medial wall and a thicker acetabular prosthesis than the patients normal medial wall, the center of rotation will of necessity be lateralized a few millimeters. This can later be factored in when planning the femoral offset.

Once the acetabular position is restored to normal with the appropriate reaming and thickness of prosthesis, the prosthesis is implanted with either cement or bony ingrowth. If using cement, care must be taken not to lateralize the cup with a bolus of cement medial to the cup. Following cup fixation and liner insertion, the acetabular distance, i.e., inset measurement, can be re-checked by repeating the steps involved in its pre-operative measurement.

Following implantation and checking of the acetabular component, the surgeon then performs the surgical procedure of preparing the femur and inserting a trial femoral component and employing the offset-inset apparatus to recheck the offset distance between the third mark and the reference point on the bridge to provide the desired post-replacement dimensions.

At this point the surgeon has the critical measurements of pre operative hip length, acetabular inset, femoral offset and proximal femoral width. Using the preoperative pelvic X Ray, adjustments can be calculated to recreate normal length and acetabular inset now changed by the erosive effect of arthritis. In the event that it was determined prior to beginning the surgical procedure that the patient's leg needed to be lengthened or shortened, then the lengthened or shortened amount may be taken into account when the calibration mark 44 is noted. Similarly greater offset may be desirable and can be obtained using the apparatus of the present invention.

The proximal femur is reamed, irrigated, flushed with epinephrine solution and plugged with a silastic plug to restrict cement in cases using cement fixation. Trial femoral prosthesis are selected to give correct intramedullary fill, femoral offset and hip length. Varying neck lengths, femoral offsets and femoral neck angles gives the surgeon greater ability to approach the normal anatomy of the hip. With each trial of the femoral prosthesis, the hip is relocated, the foot holder is applied and the length and femoral offset measurements are checked.

Figure 9:
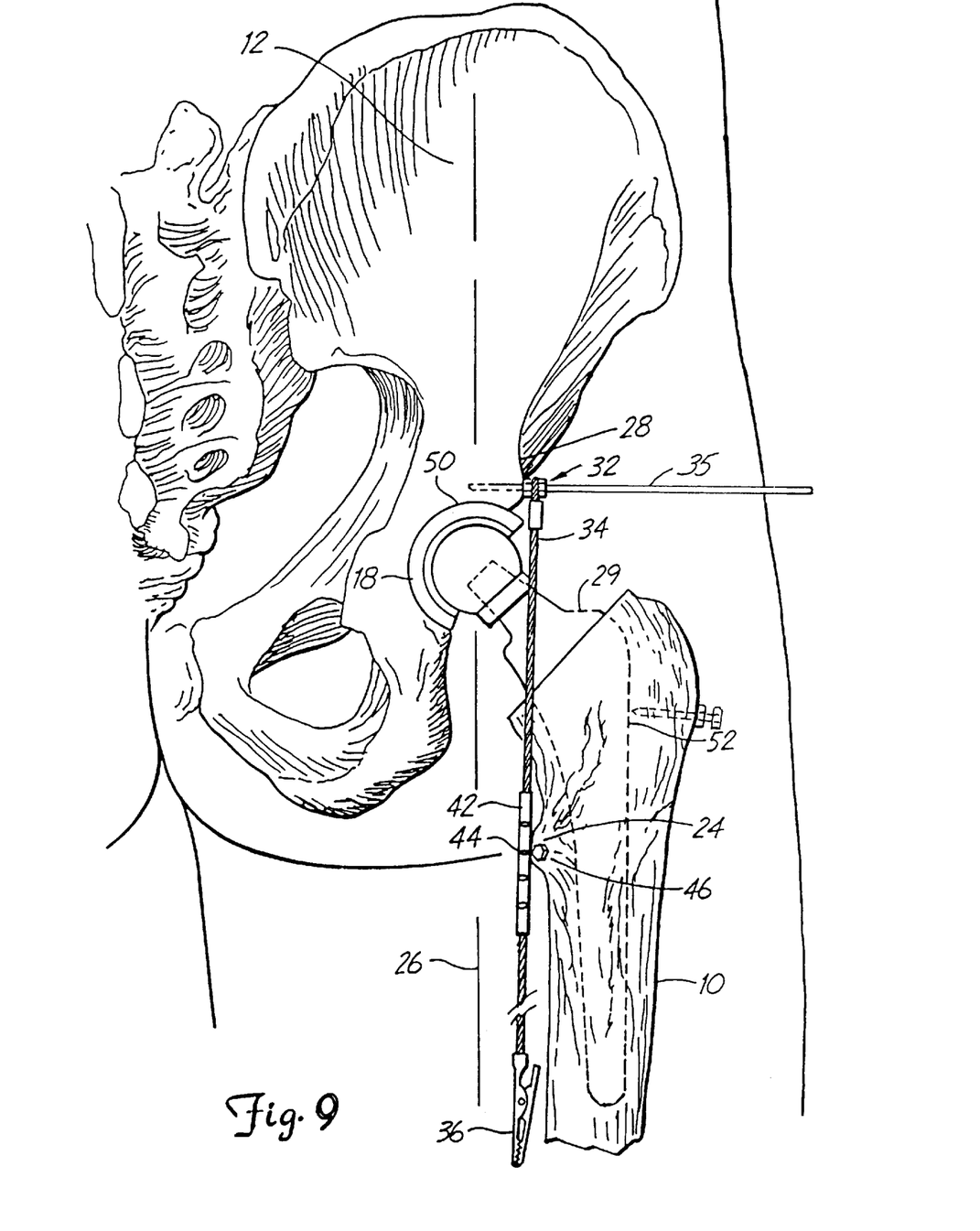
FIG. 9 is an illustration of the use of the hip length apparatus of FIG. 4 in selecting a femoral implant of the appropriate length in a posterior surgical approach.
Figure 10:
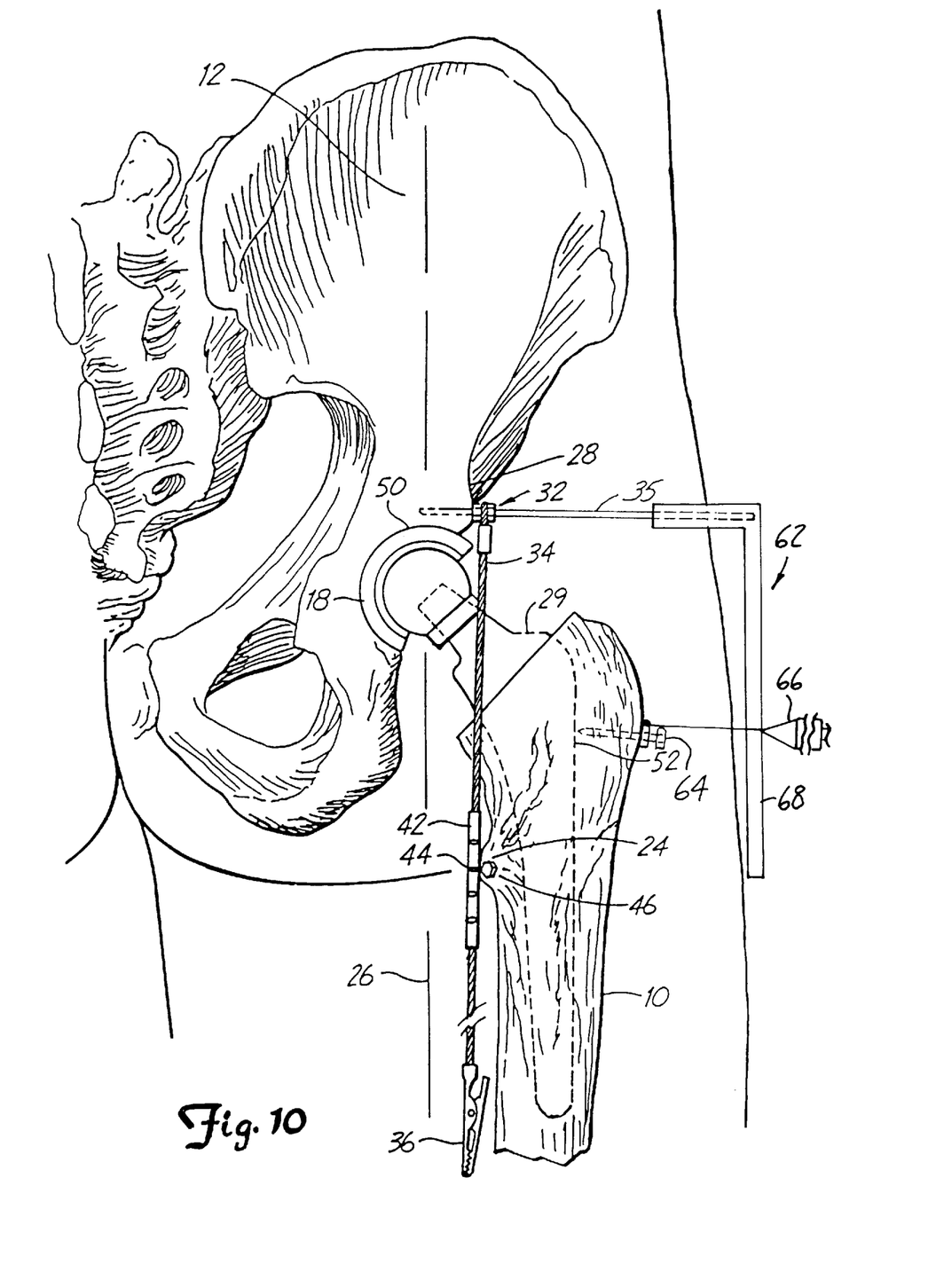
FIG. 10 is an illustration of the use of the offset-inset apparatus of FIG. 3 in selecting the appropriately sized femoral implant having the appropriate offset distance in accordance with the method of the present invention practiced in a posterior surgical approach.

In the preferred embodiment of illustrated in FIG. 9, the femoral canal 52 is reamed out, a trial femoral implant 29 is inserted as shown in FIG. 9 to test the fit and the articulation of the leg. FIG. 9 illustrates the insertion of a trial femoral implant 29 comprising the femoral implant stem 31 and femoral implant head 33 in relation to the acetabular cup prosthesis 50 and the femoral canal 52 outlined in the resected femur 10.

Both the hip length apparatus 30 and offset-inset apparatus are employed in the trial fitting stage to ensure that the selected neck length results in the desired leg length and offset. As illustrated in FIG. 9, once a trial femoral implant 29 is in place, the stranded wire cable 34 is extended in the direction of the weight supporting axis 26 to determine whether or not the calibration indicia 44 previously aligned to the mark or nail 46 is again aligned. If the measurement indicates that the actual position is superior or inferior to the desired calibration indicia 44, then the trial femoral implant 29 is withdrawn and/or longer or shorter necked components are substituted. The process is repeated until the desired calibration indicia is aligned as closely as possible to the femoral mark or nail.

When the predetermined hip length and femoral offset are obtained with selected prosthetic stem and head-neck trial components, final fixation of the permanent prosthesis is performed. Final measurements of hip length and femoral offset are recorded. The tower with the attached cable and the two marker nails are removed. The hip is checked for stability and routine closure is performed. A post operative X Ray is obtained in recovery and critically analyzed by the surgeon.

After the properly sized components are installed, the surgical nail 32 and 46 (if used) as well as the cable 34 are removed and the incision is closed in the normal manner. By use of the inventive apparatus and method, the incidence of reoperation required to correct for leg length errors is virtually eliminated. Obtaining the correct offset will lower the risk of postoperational dislocation of the hip.

Critically evaluating prosthetic hips at the time of implantation, or by later X-ray evaluation, will reveal nine different geometric joint configurations that can be used when considering length and offset. These configurations include:

correct length with correct offset
correct length with increased offset
correct length with decreased offset
short length with correct offset
short length with increased offset
short length with decreased offset
increased length with normal offset
increased length with increased offset
increased length with decreased offset In the course of measuring the length of a replacement hip, Applicant has discovered a method and apparatus that reflects the fact that the ultimate stability of the joint, as well as the surface tension of the metal on polyethylene articulation, is significantly affected by the medialization-lateralization of the center of rotation of the hip as well as the offset of the shaft of the femur.

A variety of factors are known to medialize the center of hip rotation, including arthritic erosion of the acetabulum, deep reaming by the surgeon, pelvic and acetabular fractures, and small femoral prosthetic heads.

A number of other factors are considered to lateralize the center of hip rotation, including inadequate acetabular reaming by the surgeon, overly thick acetabular prosthesis, lateralization of the acetabular prosthesis by cement, and larger femoral prosthetic heads.

Yet further factors are considered to medialize femoral offset, including medialized acetabular prosthesis, increased femoral neck angle of the prosthesis relative to the patients, excessive surgical removal of calcar-neck, excessively short femoral neck of prosthesis selected, and small diameter femoral prosthetic head.

Still other factors are considered to lateralize the femoral offset, including lateralized acetabular prosthesis, decreased femoral neck angle of prosthesis relative to the patients natural neck angle, increased inset built into the femoral neck prosthesis, inadequate surgical removal of calcar-neck, excessively long femoral neck of prosthesis selected, and larger femoral neck diameter.

Similarly, many factors can be identified as increasing the hip length, including excessive femoral neck length prosthesis selected, inadequate surgical removal of calcar-neck, greater neck angle of femoral prosthesis than the patients own neck angle, distal placement of the acetabular prosthesis, and surgeons selection of a long neck to help stabilize a loose feeling hip (usually due to inadequate offset).

Correspondingly, factors that serve to decrease the hip length include shorter femoral neck length prosthesis than the patients own neck length, excessive removal of calcar-neck, loose eroding hip prosthesis, congenital dysphasia, arthritic erosion, and previous fractures and growth disturbances.

Anatomic studies on cadavers reveal the variance in hip length between normal individuals is 41 mm (over 1 and ½ inches), the variance in hip offset is 37 mm (1 and 5 ½ inches), and the hip neck angle variance is 105 to 154 degrees (49 degrees). The surgeon can modify length and offset during surgery by a variety of techniques, however, the femoral neck angle is predetermined by most manufacturers at 135 degrees.

The term "measured hip" implies the surgeon measures and obtains correct hip length, accurate center of rotation of the hip, and desired femoral offset, thereby effectively restoring geometry of the hip as close as possible to the pre arthritic state.

It can be seen that a variety of factors interact to determine the replacement length and femoral shaft offset-inset distance. The accurate replacement of a patient's anatomic variants correctly will improve the ultimate function of the joint and likely affect surface tension which may result in reduced polyethylene debris and acetabular wear.

The invention has been described in detail with particular reference to the preferred embodiments thereof, but it will be understood that variations and modifications can be effected within the spirit and scope of the invention.

It is claimed:

1. An offset-inset apparatus useful in combination with a hip length device, the hip length device being adapted to determine pre- and post-replacement length distances between first and second fixed points along an exposed hip joint, the offset-inset apparatus being adapted to determine pre- and post-replacement distances between one or more other fixed points on the joint and corresponding reference points positioned with respect to the joint, the apparatus comprising an acetabular attachment attachable to the superior eminence of the acetabulum, a femoral attachment capable of being fixed to the femur at approximately the position of the greater trochanter, and a measuring device for measuring and noting distances between the reference points and the other fixed points, wherein the measuring device comprises a rod adapted to be attached to the acetabular attachment to provide fixed reference points with respect to the joint, and a gauge for measuring distances between the reference points and one or more fixed points on the acetabulum or femur.

2. An offset-inset apparatus according to claim 1 wherein the rod comprises first and second substantially perpendicular arms, the first arm adapted to be attached to the acetabular attachment in a manner that extends the second arm alongside and spaced away from the exposed femur, in order to provide one or more reference points with respect to fixed points on the joint.

3. An offset-inset apparatus according to claim 2 wherein the measuring device is provided in the form of a calibrated gauge for determining one or more distances between the reference points provided by the second arm and one or more other fixed points.

4. An offset-inset apparatus according to claim 3 wherein the first arm is attachable to the iliac marker of a hip length device.

5. An offset-inset apparatus according to claim 4 where the arm and iliac marker are attachable by means of a slip-fit coupling.

6. An offset-inset apparatus according to claim 4 where the arm and iliac marker are attachable by means of a male-female threaded coupling.

7. An offset-inset apparatus according to claim 4 where the arm and iliac marker are attachable by means of a serrated coupling.

8. An offset-inset apparatus according to claim 4 where the arm and iliac marker are attachable by means of a locking collar.

9. An offset-inset apparatus according to claim 1 wherein the measuring device is provided in the form of a first arm portion having calibrations thereon.

10. An offset-inset apparatus for use during reconstructive hip surgery, the apparatus being adapted to determine pre- and post-replacement distances between one or more fixed points on the joint and corresponding reference points positioned with respect to the joint, the apparatus comprising an acetabular attachment attachable to the superior eminence of the acetabulum, a femoral attachment attachable to the femur at approximately the position of the greater trochanter, and a measuring device for measuring and noting distances between the reference points and corresponding fixed points on the joint, wherein the femoral attachment comprises a nail adapted to be implanted into the femur, and the measuring device comprises a rod attachable to the acetabular attachment and comprising first and second perpendicular arms, the first arm being attachable to the acetabular attachment in a manner that positions the second arm alongside and spaced away from the exposed femur in order to provide one or more reference points with respect to fixed points on the joint.

11. An offset-inset apparatus according to claim 10 wherein the apparatus is adapted to be used in combination with a hip length device that comprises an implantable iliac marker, and the rod is adapted to be attached to the iliac marker.

12. An offset-inset apparatus according to claim 10 wherein the rod is adapted to be attached to the iliac bone.

13. An offset-inset apparatus according to claim 10 wherein the apparatus is adapted to contact a fixed point provided by the interior surface of the acetabulum.

14. An offset-inset apparatus according to claim 10 wherein the apparatus is adapted to contact a fixed point provided by the femoral attachment.

15. An offset-inset apparatus according to claim 10 wherein the apparatus is adapted to contact fixed points provided by the interior surface of the acetabulum and the femoral attachment.

* * * * *